(12) United States Patent
Smits et al.

(10) Patent No.: US 7,278,324 B2
(45) Date of Patent: *Oct. 9, 2007

(54) CARBON NANOTUBE-BASED SENSOR AND METHOD FOR DETECTION OF CRACK GROWTH IN A STRUCTURE

(75) Inventors: Jan M. Smits, Monument, CO (US); Marlen T. Kite, Hayes, VA (US); Thomas C. Moore, Poquoson, VA (US); Russell A. Wincheski, Williamsburg, VA (US); JoAnne L. Ingram, Norfolk, VA (US); Anthony N. Watkins, Hampton, VA (US); Phillip A. Williams, Suffolk, VA (US)

(73) Assignee: United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/155,923

(22) Filed: Jun. 15, 2005

(65) Prior Publication Data

US 2006/0283262 A1    Dec. 21, 2006

(51) Int. Cl.
*G01N 19/08* (2006.01)
(52) U.S. Cl. .............. 73/799; 73/774; 73/762; 73/763; 73/788; 977/972
(58) Field of Classification Search ........... 73/799, 73/774, 788, 762, 763; 977/742

See application file for complete search history.

(56) References Cited

U.S. PATENT DOCUMENTS 5,184,516 A    2/1993    Blazic et al.
(Continued)

FOREIGN PATENT DOCUMENTS

JP    11241903 A2    9/1999
(Continued)

OTHER PUBLICATIONS

Jan Smits, Buzz Wincheski, JoAnne Ingram, Neal Watkins, and Jeff Jordan. Controlled Deposition and Applied Field Alignment of Single Walled Carbon Nanotubes for CNT Device Fabrication. Mat. Res. Soc. Symp. Proc. vol. 739. (2003). Accessed online on Oct. 29, 2006. <http://www.mrs.org/s_mrs/bin.asp?CID=2557&DID=59018&DOC=FILE.PDF>.*

(Continued)

*Primary Examiner*—Michael Cygan
*Assistant Examiner*—Punam Patel
(74) *Attorney, Agent, or Firm*—Linda B. Blackburn; Kurt G. Hammerle

(57) ABSTRACT

A sensor has a plurality of carbon nanotube (CNT)-based conductors operatively positioned on a substrate. The conductors are arranged side-by-side, such as in a substantially parallel relationship to one another. At least one pair of spaced-apart electrodes is coupled to opposing ends of the conductors. A portion of each of the conductors spanning between each pair of electrodes comprises a plurality of carbon nanotubes arranged end-to-end and substantially aligned along an axis. Because a direct correlation exists between the resistance of a carbon nanotube and its strain, changes experienced by the portion of the structure to which the sensor is coupled induce a corresponding change in the electrical properties of the conductors, thereby enabling detection of crack growth in the structure.

20 Claims, 8 Drawing Sheets

U.S. PATENT DOCUMENTS

| | | |
|---|---|---|
| 5,195,046 A | 3/1993 | Gerardi et al. |
| 5,549,803 A | 8/1996 | Schoess et al. |
| 6,191,519 B1 | 2/2001 | Nye et al. |
| 6,370,964 B1 | 4/2002 | Chang et al. |
| 6,528,020 B1* | 3/2003 | Dai et al. ............. 422/98 |
| 6,564,640 B1 | 5/2003 | Allaei |
| 6,855,603 B2* | 2/2005 | Choi et al. ............ 438/268 |
| 2002/0117659 A1 | 8/2002 | Lieber et al. |
| 2002/0159943 A1 | 10/2002 | Smalley et al. |
| 2003/0089899 A1 | 5/2003 | Lieber et al. |
| 2003/0185985 A1 | 10/2003 | Bronikowski et al. |
| 2003/0218224 A1 | 11/2003 | Schlaf et al. |
| 2004/0004485 A1 | 1/2004 | Lee et al. |
| 2004/0012062 A1 | 1/2004 | Miyajima et al. |
| 2004/0228961 A1* | 11/2004 | Smits et al. ............ 427/2.13 |
| 2005/0284232 A1* | 12/2005 | Rice ....................... 73/762 |
| 2006/0010996 A1* | 1/2006 | Jordan et al. .......... 73/866.1 |

FOREIGN PATENT DOCUMENTS

| | | |
|---|---|---|
| WO | WO 02/48701 A2 | 12/2001 |
| WO | WO 02/31179 A2 | 4/2002 |
| WO | WO 03/005450 A2 | 1/2003 |

OTHER PUBLICATIONS

Chen et al., "Aligning Single-Wall Carbon Nanotubes With an Alternating-Current Electric Field," Applied Physics Letters, vol. 78 (No. 23), p. 3714-3716, (Jun. 4, 2001).

* cited by examiner

CARBON NANOTUBE-BASED SENSOR AND METHOD FOR DETECTION OF CRACK GROWTH IN A STRUCTURE

ORIGIN OF THE INVENTION

The invention described herein was made in the performance of work under a NASA contract and by an employee of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor elected not to retain title.

CROSS REFERENCE TO RELATED APPLICATION

This application is related to co-pending U.S. application Ser. No. 10/890,843 filed Jul. 13, 2004, entitled "Carbon Nanotube-Based Sensor And Method For Continually Sensing Changes In A Structure" and co-pending U.S. application Ser. No. 10/730,188 filed Dec. 4, 2003, entitled "Controlled Deposition And Alignment Of Carbon Nanotubes."

FIELD OF THE INVENTION

This invention relates to sensors and sensing methods that use carbon nanotubes. More specifically, the invention is a carbon nanotube-based sensor and method for detecting crack growth in a structure.

SUMMARY OF THE INVENTION

In accordance with the present invention, a sensor is provided for detecting changes experienced by a structure. A substrate, adapted to be coupled to a portion of a structure, has a plurality of carbon nanotube (CNT)-based conductors coupled thereto. The conductors are arranged side-by-side to one another. At least one pair of spaced-apart electrodes is coupled to opposing ends of the conductors with the conductors electrically coupling each pair of spaced-apart electrodes to one another. A portion of each of the conductors spans between each pair of spaced-apart electrodes and is defined by a plurality of carbon nanotubes arranged end-to-end and substantially aligned along an axis. During operation of the sensor, the electrical properties of the conductors are monitored first when the portion of the structure is experiencing baseline parameters to establish a baseline value. Because a change in the electrical properties of the conductors may be made to be indicative of changes in the baseline parameter of strain experienced by the portion of the structure to which the sensor is coupled, the electrical properties of the conductors are continuously monitored over time to detect crack growth.

DETAILED DESCRIPTION

Figure 1:
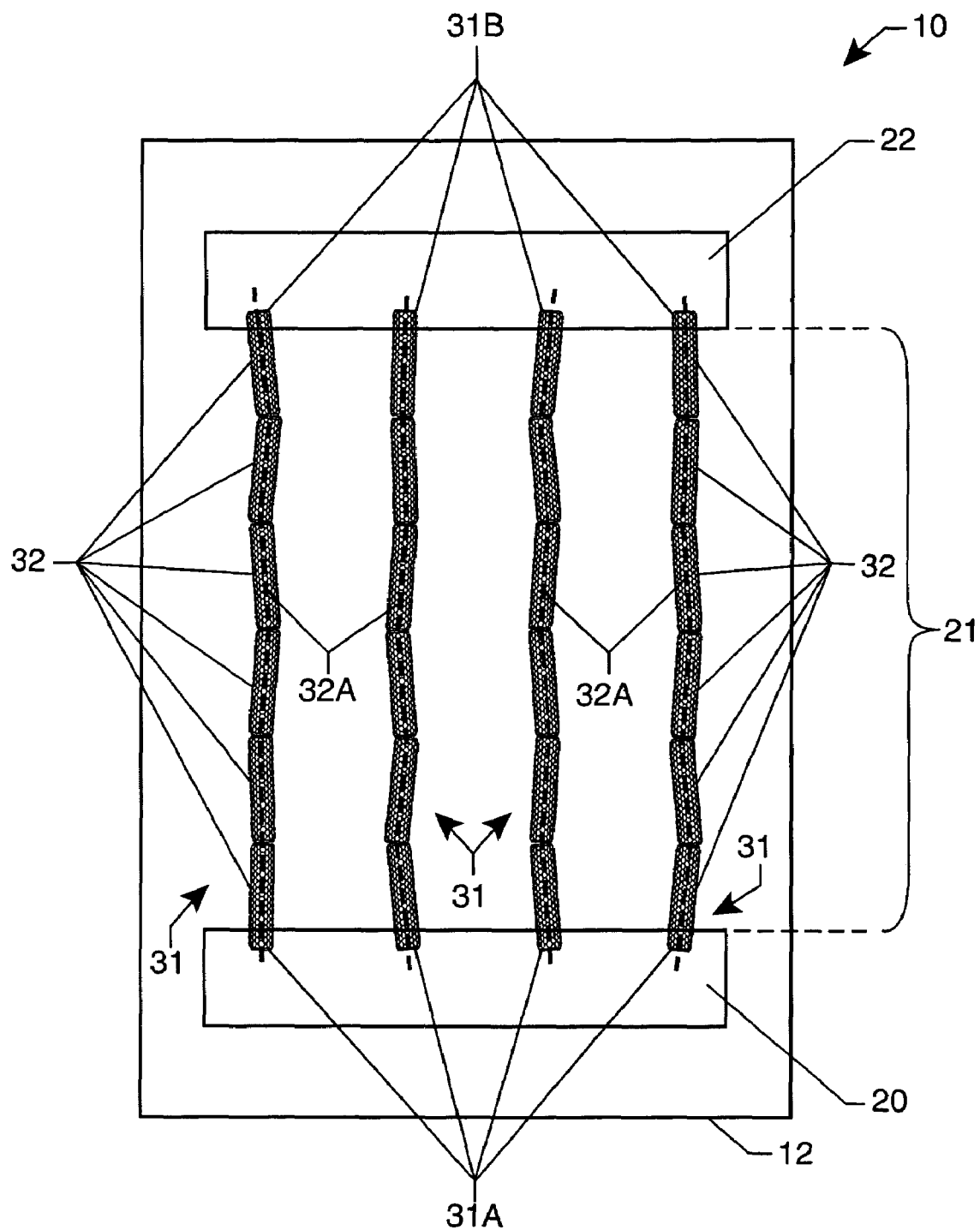
FIG. 1 is a plan view of a sensor assembly depicting aligned carbon nanotube (CNT)-based conductors, the ends of which are coupled to a pair of spaced-apart electrodes in accordance with an embodiment of the present invention.

Referring now to the drawings, and more particularly to FIG. 1, a sensor assembly in accordance with one embodiment of the present invention is shown and referenced generally by numeral 10. Sensor assembly 10 is shown and will be described herein for purposes of demonstrating the concepts of an embodiment of the present invention, but it is to be understood that the particular structure and construction of sensor assembly 10 is just one example of an embodiment.

Sensor assembly 10 includes a substrate 12 with spaced-apart electrodes, such as strips 20 and 22, positioned on substrate 12 such that portions thereof oppose one another with a gap 24 being defined therebetween. Electrodes 20 and 22 can be, but are not required to be, parallel to one another as is the case in the illustrated example.

A plurality of carbon nanotube (CNT)-based conductors 31 comprising a number of carbon nanotubes (CNTs) 32 are operatively positioned on substrate 12. Such operative positioning may include depositing the CNTs 32 directly on substrate 12, adhering the CNTs 32 to substrate 12 by means of an adhesive (not shown) interposed between the CNTs and the substrate, or otherwise coupling the CNTs 32 to substrate 12 for support thereby. Regardless of the method or system used to operatively position the CNTs 32, each conductor 31 spans gap 21 between opposing portions of electrodes 20 and 22. The plurality of CNTs 32 are arranged end-to-end and aligned to define an electrical conduction path among the aligned ones of CNTs 32 between the electrodes 20 and 22. An example of this conduction path occurs, for example, when each CNT's longitudinal (or tube) axis 32A is substantially perpendicular to electrodes 20 and 22. The carbon nanotubes positioned and aligned by the present embodiment can be single-wall or multi-wall carbon nanotubes.

Opposing ends 31A, 31B of each conductor 31 are in electrical contact with a respective one of electrodes 20, 22. For clarity of illustration, the size of CNTs 32 is greatly exaggerated and only four CNT-based conductors 31 are shown. However, as would be understood by one of ordinary skill in the art, many more such CNT-based conductors can and would most likely be present in the actual sensing device. To achieve the structure illustrated in FIG. 1, sensor assembly 10 can be constructed in accordance with the teachings of U.S. patent application Ser. No. 10/730,188, filed Dec. 4, 2003, and entitled "CONTROLLED DEPOSITION AND ALIGNMENT OF CARBON NANOTUBES," the entire contents of which are hereby incorporated by reference.

Generally, the controlled deposition and alignment of CNTs for use as a sensor occurs as follows. A CNT attraction material is deposited on a substrate in a gap region defined between two alignment electrodes on the substrate. An electric potential is applied to the two electrodes. The CNT attraction material is wetted with a solution comprising a carrier liquid having CNTs suspended therein. A portion of the CNTs align with the electric field (which, in the plane of the electrodes, is substantially perpendicular to the edges of the electrodes) and adhere to the CNT attraction material. The carrier liquid and any CNTs not adhered to the CNT attraction material are then removed, thereby leaving a structure such as the embodiment illustrated in FIG. 1.

Figure 2:
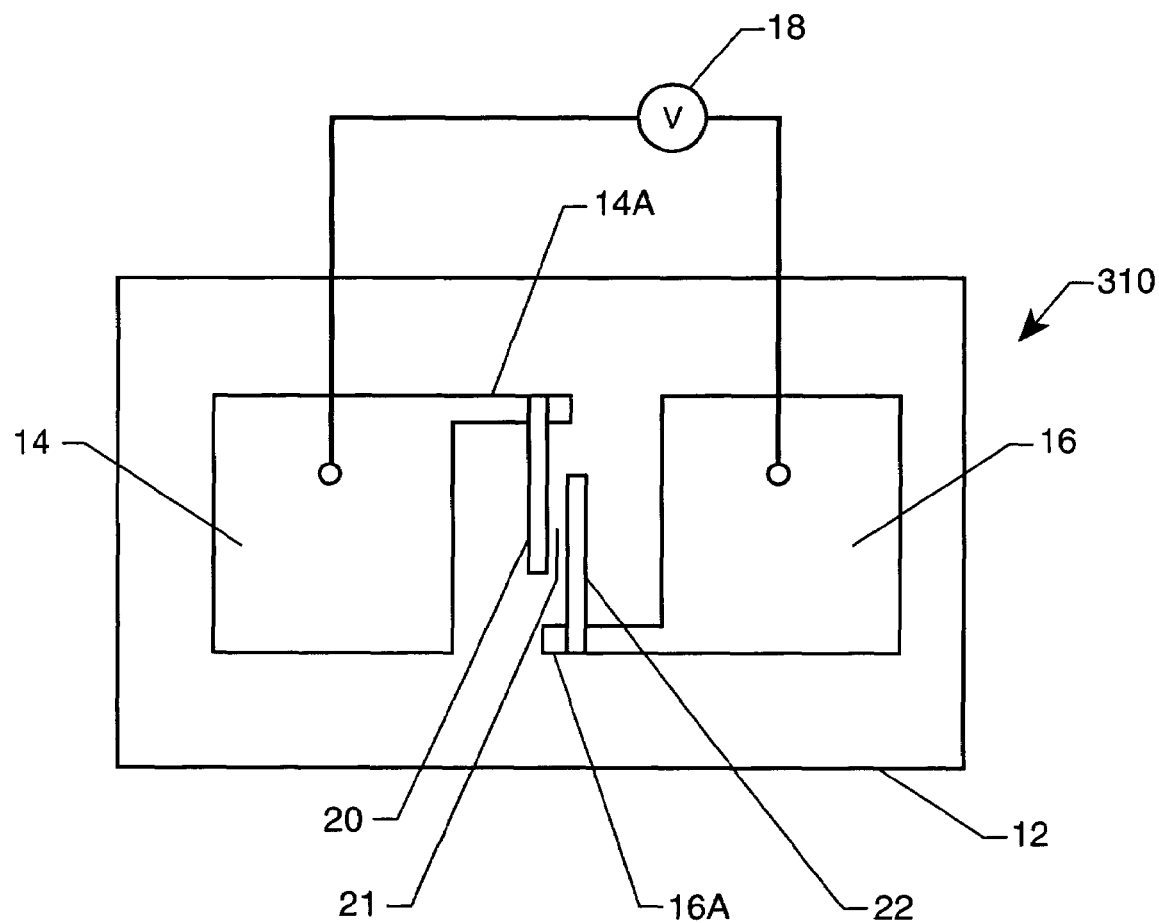
FIG. 2 is a schematic view of an apparatus used in the deposition and alignment of CNTs in accordance with an embodiment of the present invention.

Referring now to FIG. 2, an apparatus used to demonstrate the deposition and alignment of CNTs in accordance with an embodiment of an alignment electrode/CNT-based conductor assembly is shown and referenced generally by numeral 310. Apparatus 310 is shown and will be described herein for purposes of demonstrating an embodiment for construction. However, the particular structure and construction of apparatus 310 can be achieved in other ways without departing from the scope of the present invention.

Apparatus 310 includes the substrate 12 with spaced-apart electrical contact pads 14 and 16 deposited thereon. For example, in terms of many microcircuit applications, substrate 12 is a silicon wafer and contact pads 14 and 16 are any highly conductive material such as gold. Typically, each of contact pads 14 and 16 has a respective electrode contact leg 14A and 16A extending therefrom such that legs 14A and 16A oppose one another as shown. The particular size and shape of the contact pads and legs can be adapted for a particular application as would be understood by one of ordinary skill in the art. Contact pads 14 and 16 are coupled to a voltage source 18 capable of applying an electrical potential thereto. Voltage source 18 can be an alternating current (AC) or direct current (DC) source without departing from the scope of the present invention.

Electrically coupled to leg 14A is the alignment electrode 20 and electrically coupled to leg 16A is the alignment electrode 22. Electrodes 20 and 22 are deposited on substrate 12 such that portions thereof oppose one another with the gap 21 being defined therebetween. Electrodes 20 and 22 can be, but are not required to be, parallel to one another. Additional opposing pairs of electrodes or electrode strips can be provided without departing from the scope of the present embodiment.

Figure 5:
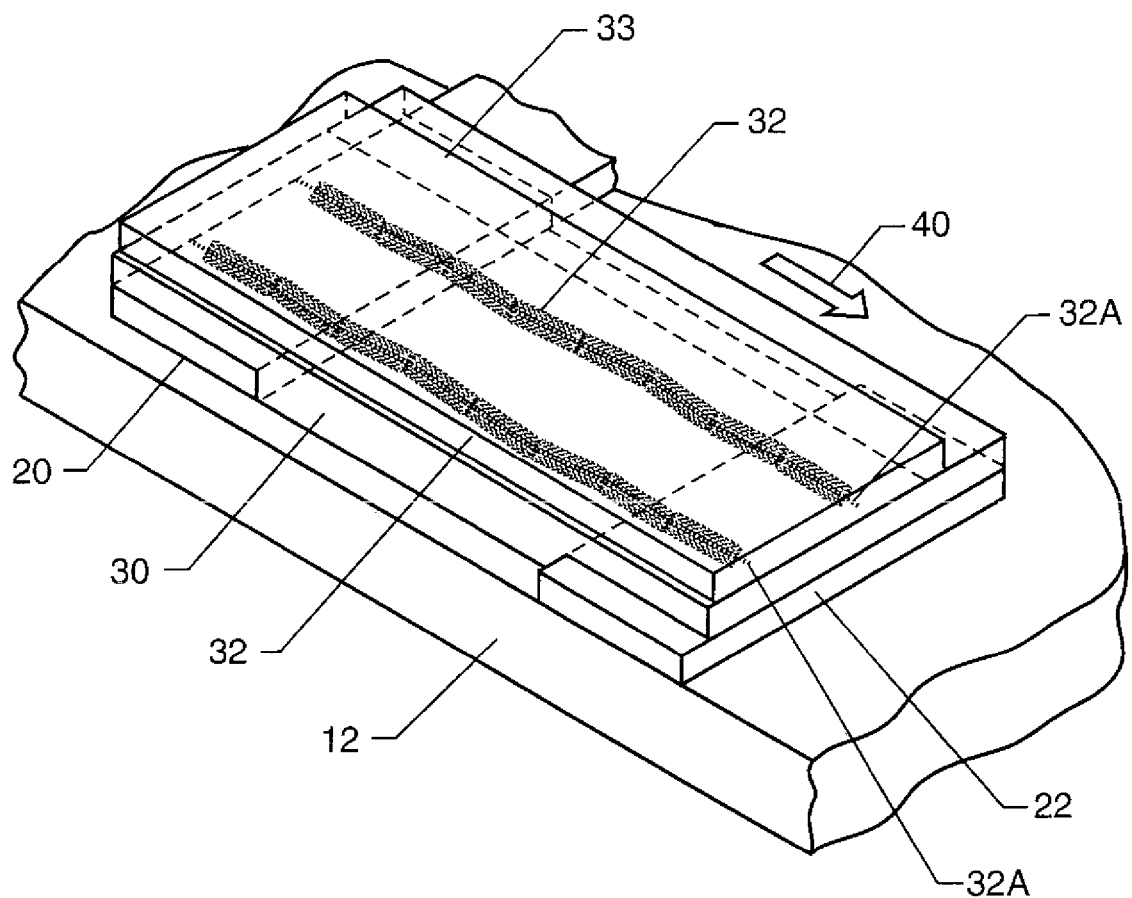
FIG. 5 is a perspective view of a portion of the apparatus in FIG. 2 depicting the CNT attraction material with the CNTs being deposited and aligned on and between the electrodes of the apparatus in accordance with another embodiment of the present invention.

In general, the method of deposition modifies apparatus 310 by (i) specific placement thereon of a material that attracts CNTs thereto, and (ii) deposition and alignment of CNTs on the specifically-placed CNT attraction material such that the CNTs provide good electrical conductivity between aligned CNTs. At a minimum, and as will be explained with reference to FIG. 3, the CNT attraction material is positioned between electrodes 20 and 22, i.e., in gap 21. However, the CNT attraction material can further be deposited on and between electrodes 20 and 22 (and beyond the electrodes if so desired) as will be explained later below with reference to FIG. 5. The CNTs deposited and aligned by the present embodiment can be single or multi-wall CNTs.

Figure 3:
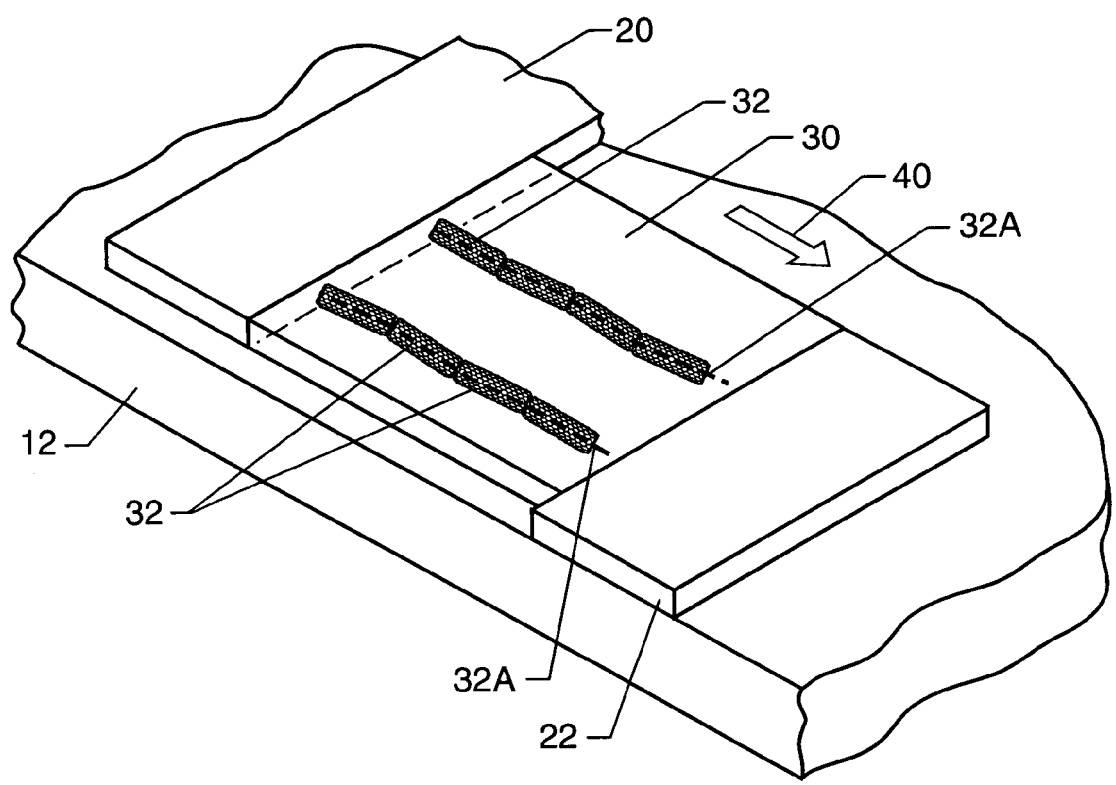
FIG. 3 is a perspective view of a portion of the apparatus in FIG. 2 depicting the CNT attraction material and CNTs deposited and aligned between the electrodes of the apparatus in accordance with an embodiment of the present invention.

Referring additionally now to FIG. 3, a perspective view of a portion of substrate 12 with electrodes 20 and 22 deposited thereon is shown. In accordance with the present embodiment, a CNT attraction material 30 is deposited in the gap between opposing portions of electrodes 20 and 22. At least one CNT 32 is coupled to material 30 and aligned such that each tube axis 32A is substantially perpendicular to electrodes 20 and 22 to define an electrical conduction path between aligned ones of CNTs 32. When the ultimate application of aligned CNTs is to use the alignment electrodes 20 and 22 along with aligned CNTs in an electrical conduction path, the aligned ones of CNTs 32 must contact each of electrodes 20 and 22. However, it is to be understood that the present embodiment does not require that aligned ones of CNTs 32 contact both electrodes 20 and 22. That is, the electrical conduction path defined by aligned ones of CNTs 32 could be used to conduct between elements (not shown) deposited on and/or across aligned ones of CNTs 32. Similarly, the aligned CNTs could be used while in contact with only one of electrodes 20 and 22.

For clarity of illustration, the size of CNTs 32 is greatly exaggerated and only two sets of aligned CNTs are shown. However, as would be understood by one of ordinary skill in the art, many more sets of aligned CNTs would be present in the actual device. Furthermore, if spacing between electrodes 20 and 22 is small (e.g., less than one micron), it is possible for a single one of CNTs 32 to span between electrodes 20 and 22.

To achieve the structure illustrated in FIG. 3, apparatus 310 is first processed to place CNT attraction material 30 in its specific desired location(s). While a variety of methods can be used to deposit CNT attraction material 30, one method will be described herein by way of an illustrative example. The area of apparatus 310 to receive CNT attraction material 30 can be spin coated with a resist material (e.g., poly(methylmethacrylate) or PMMA, polymethylglutarimide, etc.) and then patterned with an electron beam to define the desired "receive" location(s) (e.g., gap 21). After cleaning (e.g., in an oxygen plasma), CNT attraction material 30 is deposited on the surface of apparatus 310. The resist material (as well as the portion of CNT attraction material 30 deposited thereon) is then removed (e.g., using standard cleaning procedures) thereby leaving CNT attraction material only in the receive location(s) such as gap 21.

CNT attraction material 30 can be any material that suitably attracts and adheres CNTs thereto. Such a material can have an amino-terminated surface that will form a hydrogen bond with one or more hydrogen molecules found on the sidewall of a CNT. Accordingly, CNT attraction material 30 can be a monolayer material such as a self-assembled monolayer (SAM) of amino-terminated moieties.

In terms of the structure shown in FIG. 3, wherein CNT attraction material 30 adheres only to the substrate 12 between electrodes 20 and 22, an example of a commercially-available CNT attraction material is aminopropyltriethoxysilane or APTES. APTES does not bond to metal, which electrodes 20 and 22 may be made of. However, other suitable monolayers can be used without departing from the scope of the present embodiment. For example, if CNT attraction material 30 is also to be deposited and adhered to electrodes 20 and 22 (as is the case with the structure shown in FIG. 5), a thiol-type of SAM can be used.

In terms of the APTES monolayer, when it comes into contact with a silicon oxide surface (i.e., the surface of a typical substrate 12), it orients itself through a self-assembly process so that the amino (—NH2) head group is pointing away from the surface of the substrate. Several different reactions resulting in different anchoring mechanisms can occur when APTES comes into contact with carboxyl (—COO) and hydroxyl (—OH) groups on the sidewall surface of CNTs. For example, with the correct selection of CNT processing and monolayer selection, a hydrogen bond forms between the monolayer and the carboxyl/hydroxyl group in the sidewall of the CNT. The carboxyl and hydroxyl groups on the nanotube surface contain a partially negative charge, while the amino head-group on the APTES is partially positive. Thus, the charges will attract, and an electrostatic bond can form. Specifically, the electron from the APTES headgroup is partially shared with the carboxyl and/or hydroxyl group on the CNT's surface. Covalent bonds could also be created by performing an aminolysis reaction so that the carboxyl groups will form an amide (—COONH—) linkage with the monolayer, although this reaction would require the use of a catalyst.

As mentioned above, the monolayer does not need to be APTES. Any monolayer that would react with the carboxyl/hydroxyl groups on the CNT sidewall could be selected. Examples include monolayers that have a hydroxyl headgroup (e.g., hydrogen bonding with the carboxyl groups and some with the hydroxyl groups) or a carboxyl head-group (e.g., more hydrogen bonding and esterification with the hydroxyl side groups could be performed to create covalent bonds, i.e., a —COOC— bond). Also, choosing monolayers that have no reactive headgroups (e.g., octadecyltrichlorosilane or OTS) can be used to "shield" the surface from nanotube attachment. Additionally, the carboxyl/hydroxyl groups on the CNT sidewalls can be modified directly to enhance or prohibit their attachment to surfaces. For example, modifying a CNT so that the sidewall thereof is functionalized with a thiol group (—SH) would cause it to attach to a gold surface.

Figure 4:
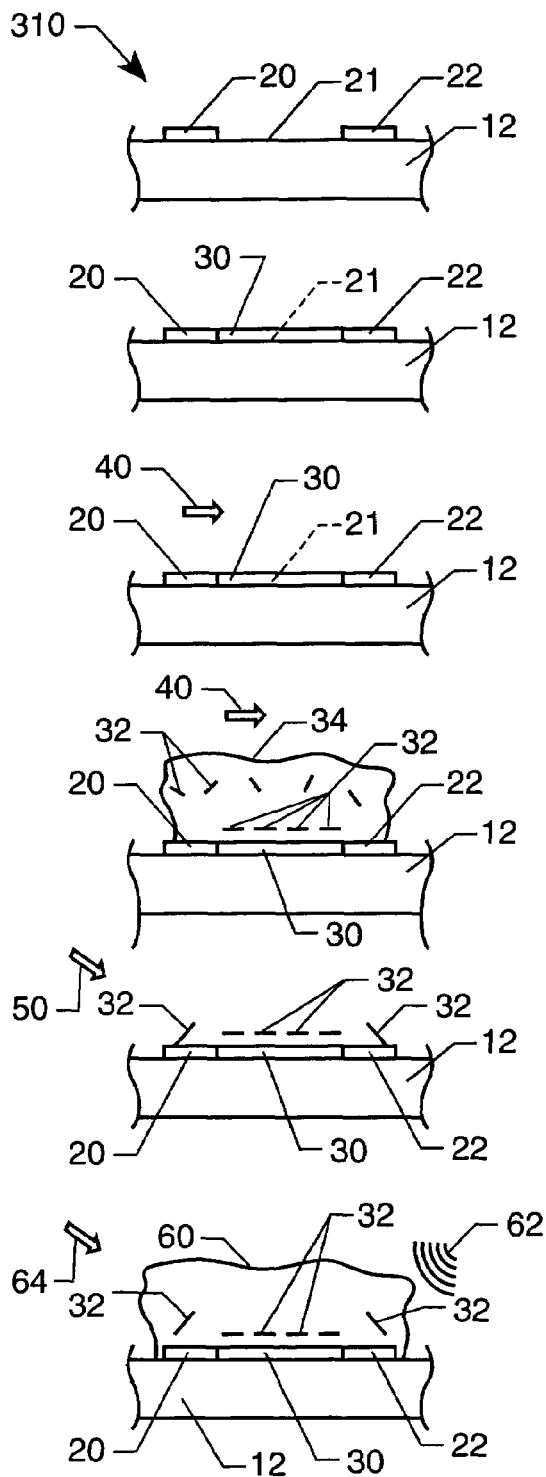
FIG. 4 schematically depicts the sequence of steps and results achieved thereby during the deposition and alignment of CNTs.
Figure 4:
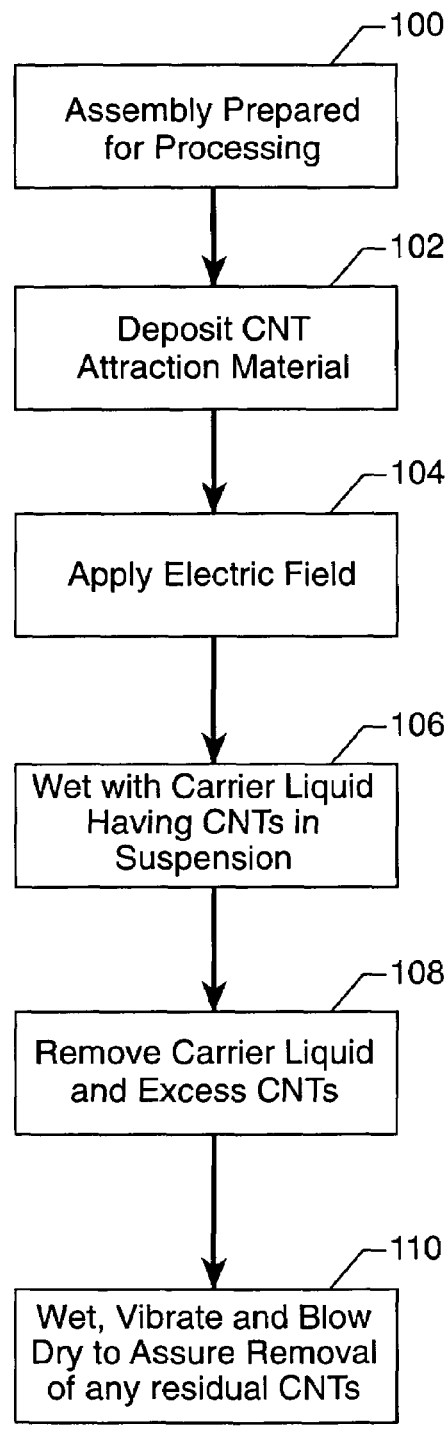

With additional reference now to FIG. 4, the sequence of steps used in the present embodiment (to create the structure shown in FIG. 3) are characterized in schematic form with a brief description thereof being provided in the corresponding box of the flowchart that is beside the description. For simplicity, a side view of only the relevant portion of apparatus 310 is shown at each step of the sequence.

At step 100, apparatus 310 is prepared for processing such that electrodes 20 and 22 are placed on substrate 12 with gap 21 defined therebetween. Once CNT attraction material 30 has been deposited in its desired location(s) at step 102, voltage source 18 is activated at step 104 so that an electric field is generated between electrodes 20 and 22 and across CNT attraction material (in gap 21) as indicated by arrow 40. To insure good alignment of CNTs 32 falling between electrodes 20 and 22, it is suggested that voltage source 18 be activated before the deposition of the solution-suspended CNTs 32 at step 106. However, for some applications it may be desirable to activate voltage source 18 at the same time as, or just after, the deposition of the solution-suspended CNTs 32. Note that the direction of electric field 40 depends on the polarity of the electric potentials applied to electrodes 20 and 22.

Next, at step 106, a quantity of CNTs 32 suspended in a carrier liquid solution 34 are deposited on apparatus 310 on and around CNT attraction material 30. Carrier liquid 34 is chosen so that the CNTs do not clump together. CNTs tend to clump together in solution due to strong van der Waals forces between individual CNTs. These forces are directly related to the size of the CNTs as well as the distance therebetween. The best solvent to disperse particular CNTs also depends on the origin of the CNTs (e.g., vendor, batch or lot, etc.) and how the CNTs have been processed (e.g., cut with nitric acid to form functionalized sidewalls, purified, etc.). Given these variables, several different solvents may be used, such as toluene, n-methylprolidone (NMP), dichloromethane (DCM), dimethylforamide (DMF), and even water that contains various surfactants (e.g., Triton X-100, sodium dodecylsulfate, and others as would be well understood in the art). In general, the carrier liquid should minimize van der Waals forces between the CNTs suspended therein. Furthermore, when mixing the CNTs in the carrier liquid, ultrasonic energy can be used to help disperse the CNTs therein.

By virtue of this process, those of the solution-suspended CNTs that come into contact with CNT attraction material 30 (i) already have their tube axis 32A substantially aligned with the direction of electric field 40 as illustrated in FIG. 3, and (ii) adhere thereto in an aligned fashion by means of hydrogen bonding with the sidewall of CNTs 32. After a brief period of time (e.g., ranging from tens of seconds to several minutes with CNT densities being proportional to exposure time), electric field 40 is removed as well as any remaining liquid solution and CNTs not adhered to CNT attraction material 30, thereby leaving CNTs 32 aligned and adhered on CNT attraction material 30 as shown in FIG. 3.

Removal of the liquid carrier and CNTs suspended therein can simply involve blowing (as indicated by arrow 50 in step 108) of an inert gas such as nitrogen across the surface of apparatus 310 (with CNT attraction material 30 and CNTs 32 deposited thereon) until dry. To assure the removal of any CNTs 32 left in areas other than on CNT attraction material 30, additional processing can be implemented at step 110. Specifically, a rinse liquid 60 (e.g., n-methylyrolidone) is washed over the apparatus as it is vibrated (e.g., sonification by acoustic wave energy 62) thereby causing the non-adhered ones of CNTs 32 to become suspended in rinse liquid 60. An inert gas (e.g., nitrogen) is then used to blow off the rinse liquid and suspended CNTs as indicated by arrow 64. As a result, the structure shown in FIG. 3 is achieved. The embodiment provides for the controlled deposition and alignment of CNTs such that their electrical conductive properties can be exploited.

As mentioned above, and as shown in FIG. 5, the final product produced by the present embodiment could have CNT attraction material 30 deposited on top of electrodes 20 and 22 as well as between them. This approach is achieved by proper selection of CNT attraction material 30 for adherence to (metal) electrodes 20 and 22 or by modifying the CNTs so that the sidewall thereof is functionalized with a thiol group (—SH) to cause it to attach to a gold (metallic) surface. With this alternate embodiment, the processing steps for achieving this structure are substantially identical to that described above. If electrical contact is desired between electrodes 20 and 22 and ones of CNTs 32 positioned thereover, an additional step of ultraviolet ozone cleaning can be applied to the appropriate areas on electrodes 20 and 22 after removal of the carrier liquid and excess CNTs.

Figure 6:
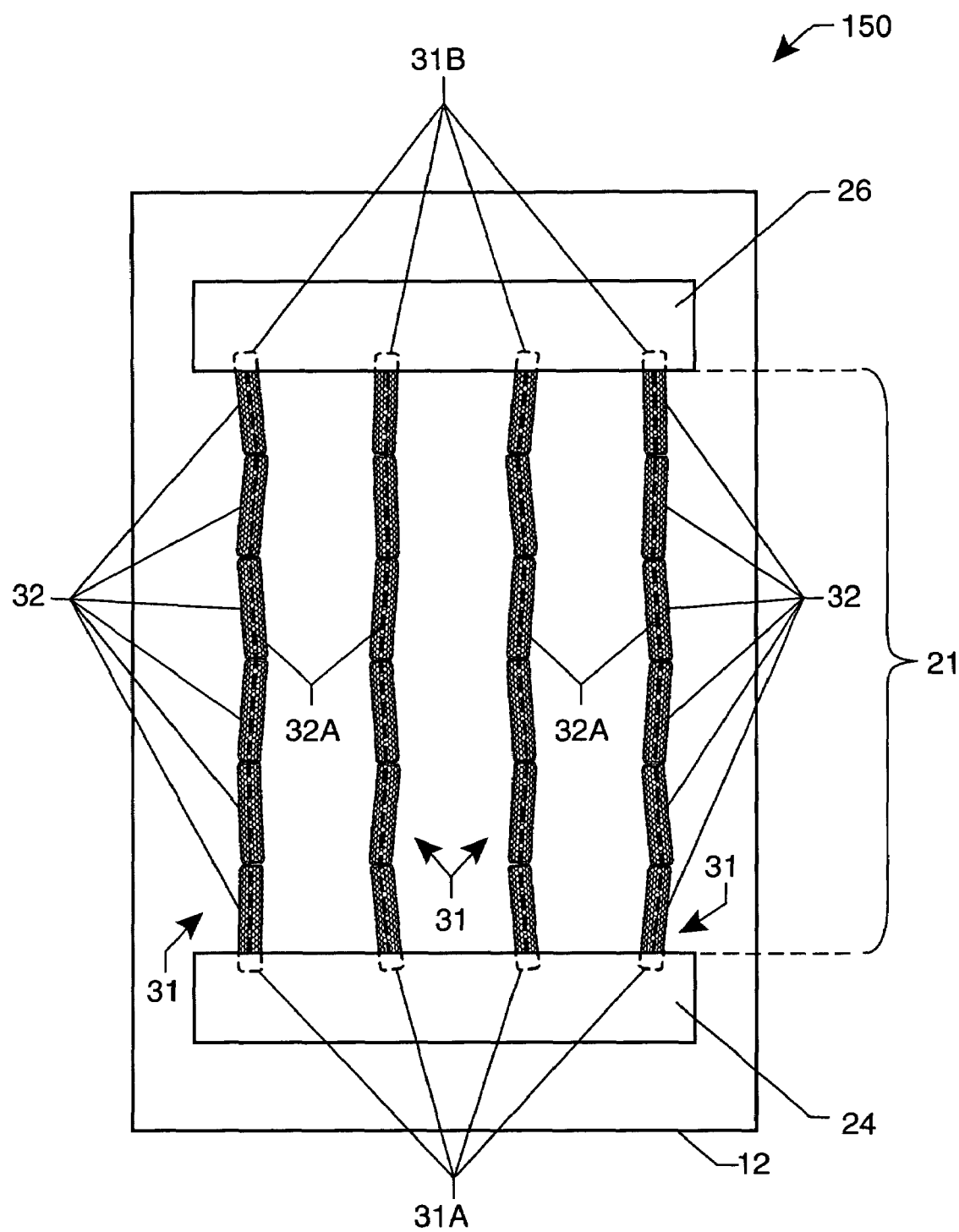
FIG. 6 is a plan view of another sensor assembly depicting aligned CNT-based conductors, the ends of which are coupled to a pair of spaced-apart electrodes on top of the CNT-based conductors in accordance with another embodiment of the present invention.
Figure 7:
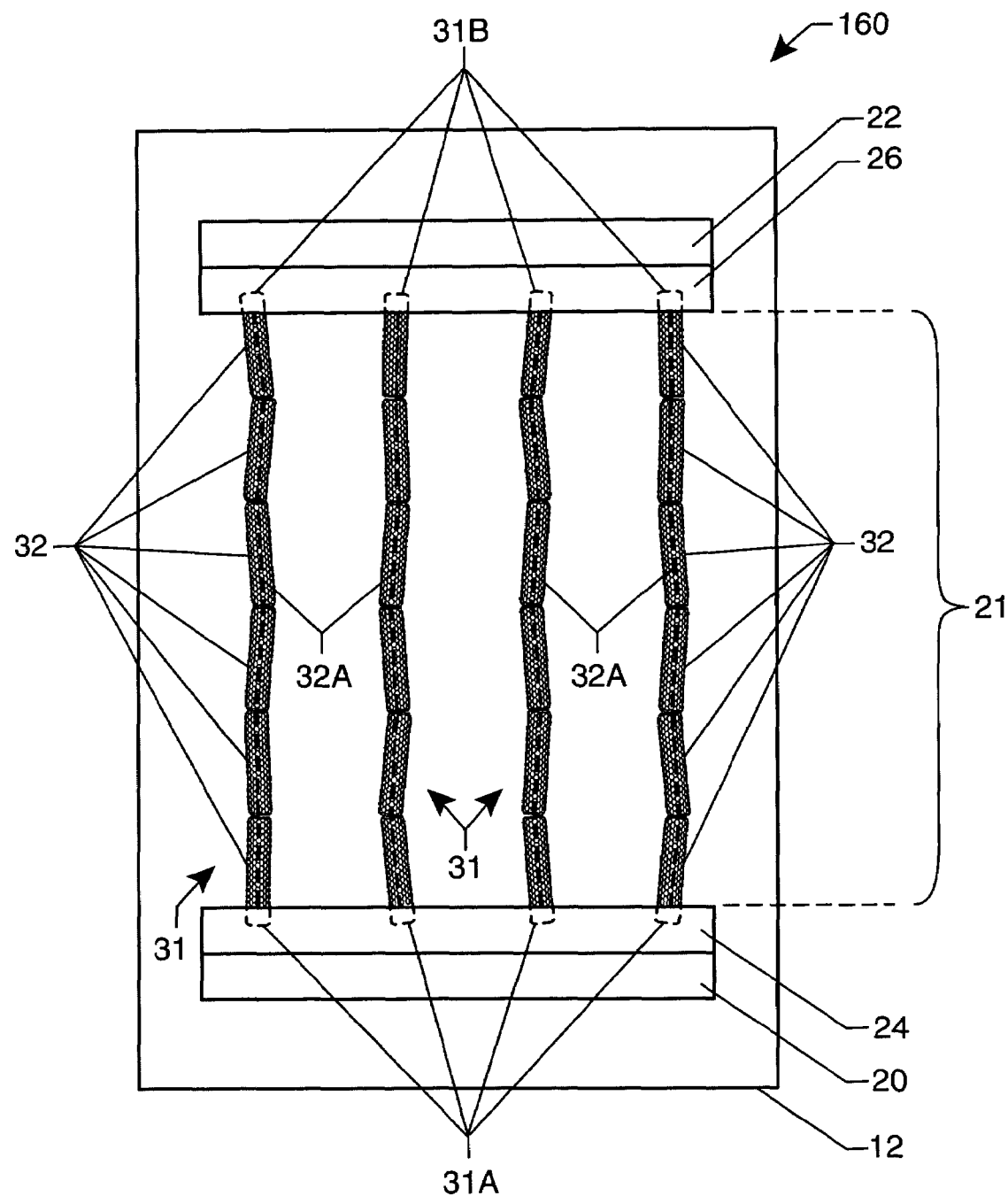
FIG. 7 is a plan view of another sensor assembly depicting aligned CNT-based conductors, the ends of which are sandwiched between electrodes in accordance with still another embodiment of the present invention.

The teachings of U.S. patent application Ser. No. 10/730,188 can be utilized to position CNT-based conductors 31 such that they are coupled on one end 31A to electrode 20 and on the other end 31B to electrode 22 in a number of different ways as illustrated in FIGS. 1, 6, and 7. (For clarity of illustration, FIGS. 1, 6, and 7 omit the CNT attraction material 30). For example, FIG. 6 illustrates a sensor assembly 150 having electrodes 24 and 26 positioned onto the opposing ends 31A, 31B, respectively, of a set of CNT-based conductors 31. This type of construction allows electrodes 24 and 26 to anchor the opposing ends 31A, 31B of each CNT-based conductor 31 in place on substrate 12. This type of construction may be employed when "sheets" of substrate 12/conductors 31 are manufactured without the electrodes 20, 22 attached thereto. The conductor "sheets" are cut into appropriately sized and shaped pieces, and subsequently have electrode material deposited thereon to make the sensor assembly. FIG. 7 illustrates a sensor assembly 160 having both electrodes 20/22 and electrodes 24/26 essentially "sandwiching" the opposing ends of CNT-based conductors 31. The use of two electrode pairs provides for redundant interrogation of CNT-based conductors 31.

Each of the above-described sensor assemblies can be used to monitor strain, pressure or temperature changes experienced by a structure to which the sensor assembly is coupled. The structure can be dynamic in nature (e.g., air, space, water or land craft) or static in nature (e.g., building, bridge, etc.). Typically, substrate 12 is coupled to a portion of a structure that is to be monitored with the sensor assembly being capable of monitoring changes at that portion of the structure. Substrate 12 may be part of the structure itself provided CNT-based conductors 30 can be deposited thereon. The sensor assembly can be optimized to monitor specific types of change. For example, if changes in a structure's strain experience are of concern, substrate 12 can be made from a flexible material such as a polymer (e.g., polyimide, polyethylene terephthalate, polyimide with copper embedded therein, etc.) or an elastomer. If the sensor assembly is to be optimized for monitoring pressure and/or temperature changes, substrate 12 could be made from an inflexible material (e.g., silicon, silicon dioxide, diamond-like-carbon or DLC, etc.). If the sensor assembly were to be optimized for temperature alone, substrate 12 could be made from an inflexible material and the CNT-based conductor portion of the assembly could be coated with a rigid, air-impermeable membrane 33 to eliminate pressure sensitivity.

Figure 8:
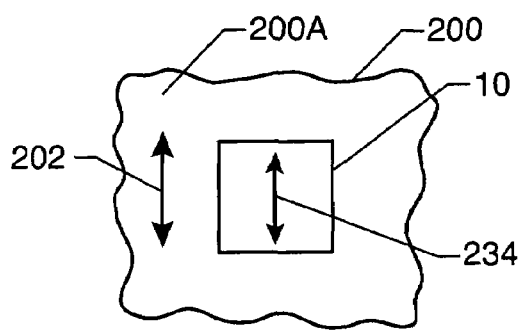
FIG. 8 is a plan view of a portion of the surface of a structure with a single sensor assembly coupled to the surface of the structure.

Referring now to FIGS. 8-12, several installation configurations of the sensor assembly(ies) are shown. FIG. 8 shows one sensor assembly (e.g., sensor assembly 10) coupled to an outer skin or surface 200A of a structure 200. A two-headed arrow 234 is used to illustrate the tube alignment direction (i.e., the substantial direction of the tube axis 32A shown in FIGS. 1, 6, and 7) for the CNT-based conductors of sensor assembly 10. Thus, in terms of monitoring changes in strain experienced by surface 200A of structure 200, sensor assembly 10 will be sensitive to strain experienced along a direction 202 (the axis of sensitivity) that is substantially parallel to tube alignment direction 234.

Figure 9:
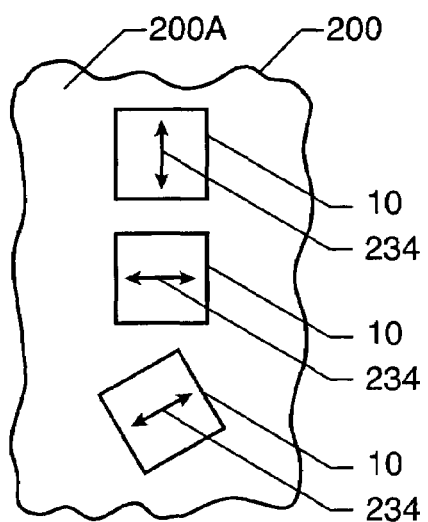
FIG. 9 is a plan view of a portion of the surface of a structure with a plurality of sensor assemblies coupled to the surface of the structure.
Figure 10:
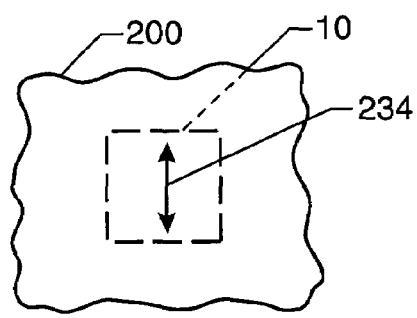
FIG. 10 is a plan view of a portion of the surface of a structure with a single sensor assembly embedded within the structure as indicated by its dashed line outline.
Figure 11:
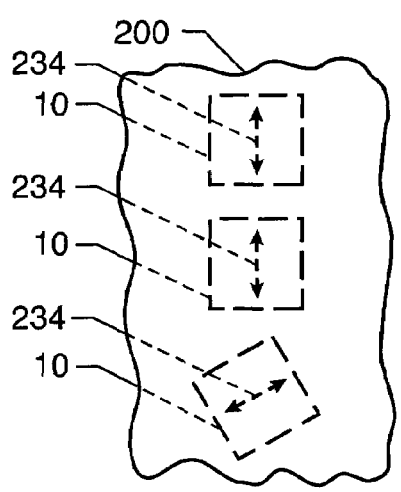
FIG. 11 is a plan view of a portion of the surface of a structure with a plurality of sensor assemblies embedded within the structure as indicated by their dashed line outlines.
Figure 12:
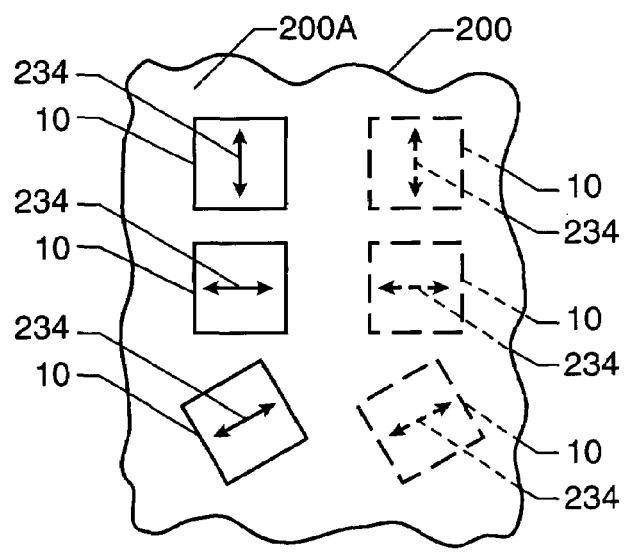
FIG. 12 is a plan view of a portion of the surface of a structure with a plurality of sensor assemblies coupled to the surface of the structure and a plurality of sensor assemblies embedded within the structure as indicated by their dashed line outlines.

A plurality of sensor assemblies 10 could also be applied/coupled to surface 200A of structure 200 as illustrated in FIG. 9 where the tube alignment direction 234 of each assembly 10 is oriented uniquely to provide for strain measurements along different axes. Still further, installation of one (FIG. 10) or more (FIG. 11) sensor assemblies 10 can be made within (i.e., embedded in) structure 200 to monitor internal strain, pressure, or temperature changes. FIG. 12 illustrates an embodiment in which sensor assemblies 10 are mounted both on surface 200A and within structure 200 with their respective tube alignment directions 234 oriented at different angles.

The process of monitoring changes experienced by a structure involves coupling one or more of the above-described sensor assemblies to a structure at the place or places of interest. Once positioned, each sensor assembly is electrically interrogated by means of an AC or DC voltage applied to each sensor's electrode pair. Connectivity for electrical interrogation may be accomplished by a Zero Insertion Force (ZIF) connector. Such electrical interrogation is performed while the structure is experiencing known or baseline levels of strain, pressure and/or temperature conditions so that the electrical properties (e.g., conductance, capacitance, inductance, etc.) of the CNT-based conductors for a sensor assembly (10, 50, or 60) are indicative of the known baseline conditions. Sensors optimized for different parameters can be utilized at the same time. After baseline conditions are established, the electrical properties of each sensor assembly are continuously monitored over time. Because a direct correlation exists between resistance of a carbon nanotube and carbon nanotube strain, changes in the electrical properties of a sensor assembly are indicative of changes in one or more of the parameters of strain, pressure, and temperature experienced by the structure, depending upon how each sensor was optimized. In terms of dynamic structures, such monitoring could occur during use whereas monitoring of static structures could run continually throughout the life of the structure.

The combination of multiple CNT-based conductors and the multiple CNT structure of each such CNT-based conductor provides the basis for operation of a robust sensor assembly. Specifically, the use of multiple CNTs aligned and arranged end-to-end form an electrical conductor that is strong yet flexible. The bonds between adjacent CNTs may be stressed during times of mechanical strain and thereby affect the electrical properties thereof. Once the strain is removed, the CNT-based conductors tend to "relax" and return to their baseline state. The ability of each CNT-based conductor to "stretch" in this fashion also enables the monitoring of gradual change in electrical properties.

The ability to monitor gradual change in electrical properties enables evaluating long-term structural fatigue and detection of crack growth by monitoring the mechanical strain field of the structure. As mentioned earlier, multiple sensor assembly groupings, such as a single triplet grouping of the sensor assemblies of FIG. 9 or 11 or the dual triplet groupings shown in FIG. 12, have different orientations or tube alignment directions 234 for each sensor assembly, with the sensor assemblies of each grouping being positioned substantially near one another, i.e. in a close arrangement, so as to enable measurement of the two-dimensional strains occurring at a specific location in multiply different directions (axial, transverse, etc.) Such strain, when appropriately mapped, may be indicative of the development of crack growth. To accomplish the level of strain mapping necessary to monitor crack growth, a plurality of the triplet groupings shown in FIG. 9 or 11 may be used to provide a dense, ordered arrangement, such as the dual triplet grouping of FIG. 12. In such an embodiment, the plurality of triplet groupings may be read together, basically enabling a strain or crack growth "camera" that maps the total strain occurring over a region of interest. Techniques available to develop the electrode patterns necessary for such close groupings or for such dense, ordered arrays of triplet groupings include photolithography coupled with electron beam lithography.

Each CNT-based sensor assembly of the triplet grouping is positioned on a flexible substrate such that the substrate of the sensor assembly flexes with the strain and the growth of a crack line or crack lines in the structure that is being monitored. Further, to eliminate or at least reduce the effects of other parameters, such as pressure, from impacting the measurement of mechanical strain, the CNT-conductor portion of sensor assembly 10 is coated with a rigid gas-impermeable membrane.

Strain mapping of the structure is accomplished during the step of electrical interrogation (which is AC or DC voltage that is applied to the electrode pair of each sensor assembly as previously described) by individually addressing each CNT-based sensor assembly or grouping of sensor assemblies in an ordered matrix. To individually address each CNT-based sensor assembly or grouping of sensor assemblies (i.e., each pixel), electrical multiplexing, as is understood by the skilled artisan, may be used. The electrical multiplexing used for a digital camera to read the individual pixels of a CCD or other light sensitive chip for image gathering is one example. This methodology comprises use of fast switching devices or other multiplexers capable of reading several different signals serially, i.e., one at a time.

The use of multiple CNT-based conductors provides redundancy in cases where one or more of the conductors fail under extreme conditions. In terms of monitoring pressure and/or temperature changes, the CNT-based conductors have a high-degree of electron transfer sensitivity, thereby providing the ability to monitor even small changes experienced by a structure.

Potential structures for coupling or embedding of the sensor assemblies include air, space, and ground vehicles. Automotive applications include measurement of engine torque conversion and vehicle compartment noise. Other automotive applications include air-bag triggers (e.g., strain sensor arrays in vehicle crumple zones) and passenger seat temperature/pressure sensors.

Potential civil engineering structures for coupling or embedding of the sensor assemblies include bridges and buildings. Civil engineering applications include testing new configurations and materials for robustness, monitoring the effects of meteorological events, and retrofitting existing buildings with surface sensors to monitor potential areas for integrity failure and initiate building evacuation if appropriate.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function and step-plus-function clauses are intended to cover the structures or acts described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed as new and desired to be secured by letters Patent of the United States is:

1. A method of detecting crack growth experienced by a structure, said method comprising the steps of:
    positioning a plurality of carbon nanotube (CNT)-based sensors into a close grouping on a portion of the structure, each said sensor comprising (i) a substrate adapted to be coupled to the portion of the structure, said substrate being flexible such that strain experienced by the portion of the structure causes relative strain in said substrate, (ii) a plurality of carbon nanotube (CNT)-based conductors operatively positioned on said substrate and arranged side-by-side to one another, said plurality of CNT-based conductors being coated with a gas-impermeable membrane to reduce pressure sensitivity of said plurality of CNT-based conductors, and (iii) at least one pair of spaced-apart electrodes electrically coupled to opposing ends of said plurality of CNT-based conductors with a portion of each of said plurality of CNT-based conductors spanning between each pair of said spaced-apart electrodes comprising a plurality of carbon nanotubes arranged end-to-end and substantially aligned along an axis;
    monitoring electrical properties of said plurality of CNT-based sensors when the portion of the structure is experiencing baseline levels of the parameter of strain to establish a baseline response; and
    continually monitoring the electrical properties over time to identify any change in the electrical properties from the baseline response, wherein a change in the electrical properties of said plurality of CNT-based sensors is indicative of crack growth experienced by the portion of the structure.

2. A method according to claim 1 wherein said step of positioning comprises the step of coupling said plurality of CNT-based sensors to a surface of the structure.

3. A method according to claim 1 wherein each of said plurality of carbon nanotubes is a single-wall carbon nanotube.

4. A method of detecting crack growth experienced by a structure, said method comprising the steps of:
    embedding a plurality of carbon nanotube (CNT)-based sensors into a close grouping in a portion of the structure, each said sensor comprising (i) a substrate adapted to be coupled to the portion of the structure, said substrate being flexible such that strain experienced by the portion of the structure causes relative strain in said substrate, (ii) a plurality of carbon nanotube (CNT)-based conductors operatively positioned on said substrate and arranged side-by-side to one another, said plurality of CNT-based conductors being coated with a gas-impermeable membrane to reduce pressure sensitivity of said plurality of CNT-based conductors, and (iii) at least one pair of spaced-apart electrodes electrically coupled to opposing ends of said plurality of CNT-based conductors with a portion of each of said plurality of CNT-based conductors spanning between each pair of said spaced-apart electrodes comprising a plurality of carbon nanotubes arranged end-to-end and substantially aligned along an axis;
    monitoring electrical properties of said plurality of CNT-based sensors when the portion of the structure is experiencing baseline levels of the parameter of strain to establish a baseline response; and continually monitoring the electrical properties over time to identify any change in the electrical properties from the baseline response, wherein a change in the electrical properties of said plurality of CNT-based sensors is indicative of crack growth experienced by the portion of the structure.

5. A method according to claim 4 wherein said step of embedding further comprises the steps of:
embedding a portion of said plurality of CNT-based sensors in the structure; and
coupling a remainder of said plurality of CNT-based sensors to a surface of the structure.

6. A method of detecting crack growth experienced by a structure, said method comprising the steps of:
positioning a plurality of carbon nanotube (CNT)-based sensors into a close grouping on a portion of the structure, including arranging said plurality of CNT-based sensors such that the axis of sensitivity associated with each one of said CNT-based sensors is at an orientation unique to the axis of sensitivity of each of the other of said CNT-based sensors within the close grouping of CNT-based sensors, each said sensor comprising (i) a substrate adapted to be coupled to the portion of the structure, said substrate being flexible such that strain experienced by the portion of the structure causes relative strain in said substrate, (ii) a plurality of carbon nanotube (CNT)-based conductors operatively positioned on said substrate and arranged side-by-side to one another, said plurality of CNT-based conductors being coated with a gas-impermeable membrane to reduce pressure sensitivity of said plurality of CNT-based conductors, and (iii) at least one pair of spaced-apart electrodes electrically coupled to opposing ends of said plurality of CNT-based conductors with a portion of each of said plurality of CNT-based conductors spanning between each pair of said spaced-apart electrodes comprising a plurality of carbon nanotubes arranged end-to-end and substantially aligned along an axis;
monitoring electrical properties of said plurality of CNT-based sensors when the portion of the structure is experiencing baseline levels of the parameter of strain to establish a baseline response; and
continually monitoring the electrical properties over time to identify any change in the electrical properties from the baseline response, wherein a change in the electrical properties of said plurality of CNT-based sensors is indicative of crack growth experienced by the portion of the structure.

7. A method according to claim 6 wherein said step of continually monitoring the electrical properties comprises individually addressing each of said close groupings of CNT-based sensors in an ordered matrix.

8. A method of detecting crack growth experienced by a structure, said method comprising the steps of:
positioning a plurality of carbon nanotube (CNT)-based sensors into a close grouping on a portion of the structure, each said sensor comprising (i) a substrate adapted to be coupled to the portion of the structure, said substrate being flexible such that strain experienced by the portion of the structure causes relative strain in said substrate, (ii) a plurality of carbon nanotube (CNT)-based conductors operatively positioned on said substrate and arranged side-by-side to one another, said plurality of CNT-based conductors being coated with a gas-impermeable membrane to reduce pressure sensitivity of said plurality of CNT-based conductors, and (iii) at least one pair of spaced-apart electrodes electrically coupled to opposing ends of said plurality of CNT-based conductors with a portion of each of said plurality of CNT-based conductors spanning between each pair of said spaced-apart electrodes comprising a plurality of carbon nanotubes arranged end-to-end and substantially aligned along an axis;
monitoring elcetrical properties of said plurality of CNT-based sensors when the portion of the structure is experiencing baseline levels of the parameter of strain to establish a baseline response; and
continually monitoring the electrical properties over time, including individually addressing each one of said CNT-based sensors in an ordered matrix, to identify any change in the electrical properties from the baseline response, wherein a change in the electrical properties of said plurality of CNT-based sensors is indicative of crack growth experienced by the portion of the structure.

9. A sensor for detecting crack growth in a structure, comprising:
a flexible substrate adapted to be coupled to a portion of the structure;
a plurality of carbon nanotube (CNT)-based conductors operatively positioned on said substrate and arranged side-by-side to one another, said plurality of CNT-based conductors being coated with a gas-impermeable membrane to reduce pressure sensitivity of said plurality of CNT-based conductors; and,
at least one pair of spaced-apart electrodes, each of said at least one pair of spaced-apart electrodes being coupled to opposing ends of at least one CNT-based conductor, said at least one CNT-based conductor electrically coupling such spaced-apart electrodes to one another;
a portion of each of said plurality of CNT-based conductors spanning between each pair of said spaced-apart electrodes comprising a plurality of carbon nanotubes arranged end-to-end and substantially aligned along an axis, wherein growth of a crack line experienced by the portion of the structure induces a change in electrical properties of said plurality of CNT-based conductors.

10. A sensor as in claim 9 wherein at least one of said pair of spaced-apart electrodes comprises two spaced-apart electrode strips positioned on said substrate, with said plurality of CNT-based conductors being positioned on said two spaced-apart electrode strips at the opposing ends of each CNT-based conductor.

11. A sensor as in claim 9 wherein at least one of said pair of spaced-apart electrodes comprises two spaced-apart electrode strips positioned on the opposing ends of each of said plurality of CNT-based conductors.

12. A sensor as in claim 9 wherein at least one of said pair of spaced-apart electrodes comprises:
a first pair of spaced-apart electrode strips positioned on said substrate, with said plurality of CNT-based conductors being positioned on said first pair of spaced-apart electrode strips at the opposing ends of each CNT-based conductor; and
a second pair of spaced-apart electrode strips positioned on the opposing ends of each of said plurality of CNT-based conductors.

13. A sensor as in claim 9 wherein each of said plurality of carbon nanotubes is a single-wall carbon nanotube.

14. A sensor as in claim 9 wherein each of said pair of spaced-apart electrodes comprises parallel electrode strips.

15. A sensor as in claim 9 wherein the CNT-based conductors are arranged substantially parallel to one another.

16. A sensor as in claim 9 further comprising a CNT attraction material deposited on said substrate among at least one of said pairs of said spaced-apart electrodes.

17. A sensor assembly for detecting crack growth experienced by a structure, comprising:
  a plurality of carbon nanotube (CNT)-based sensors positioned into a close grouping on a portion of the structure, each of said CNT-based sensors comprising (i) a substrate adapted to be coupled to the portion of the structure, said substrate being flexible such that strain experienced by the portion of the structure causes relative strain in said substrate, (ii) a plurality of carbon nanotube (CNT)-based conductors operatively positioned on said substrate and arranged side-by-side to one another, said plurality of CNT-based conductors being coated with a aas-imnermeable membrane to reduce pressure sensitivity of said plurality of CNT-based conductors, and (iii) at least one pair of spaced-apart electrodes electrically coupled to opposing ends of said plurality of CNT-based conductors with a portion of each of said plurality of CNT-based conductors spanning between each pair of said spaced-apart electrodes comprising a plurality of carbon nanotubes arranged end-to-end and substantially aligned along an axis; and
  means for monitoring the electrical properties of said plurality of CNT-based sensors over time so as to establish a baseline response when the portion of the structure is experiencing baseline levels of the parameter of strain and to identify any change in the electrical properties from the baseline response, wherein a change in the electrical properties of said plurality of CNT-based sensors is indicative of crack growth experienced by the portion of the structure.

18. A sensor assembly for detecting crack growth experienced by a structure, comprising:
  a plurality of carbon nanotube (CNT)-based sensors positioned into a close grouping on a portion of the structure, each of said CNT-based sensors comprising (i) a substrate adapted to be coupled to the portion of the structure, said substrate being flexible such that strain experienced by the portion of the structure causes relative strain in said substrate, (ii) a plurality of carbon nanotube (CNT)-based conductors operatively positioned on said substrate and arranged side-by-side to one another, said plurality of CNT-based conductors being coated with a gas-impermeable membrane to reduce pressure sensitivity of said plurality of CNT-based conductors, and (iii) at least one pair of spaced-apart electrodes electrically coupled to opposing ends of said plurality of CNT-based conductors with a portion of each of said plurality of CNT-based conductors spanning between each pair of said spaced-apart electrodes comprising a plurality of carbon nanotubes arranged end-to-end and substantially aligned along an axis; and
  means for monitoring the electrical properties of said plurality of CNT-based sensors over time so as to establish a baseline response when the portion of the structure is experiencing baseline levels of the parameter of strain and to identify any change in the electrical properties from the baseline response, wherein said means for monitoring includes individually addressing each one of said CNT-based sensors in an ordered matrix, and wherein a change in the electrical properties of said plurality of CNT-based sensors is indicative of crack growth experienced byte portion of the structure.

19. A sensor assembly for detecting crack growth experienced by a structure, comprising:
  a plurality of carbon nanotube (CNT)-based sensors positioned into a close grouping on a portion of the structure, wherein said plurality of CNT-based sensors are positioned such that the axis of sensitivity associated with each one of said CNT-based sensors is at an orientation unique to the axis of sensitivity of each of the other of said CNT-based sensors for the close grouping of plurality of CNT-based sensors. each of said CNT-based sensors comprising (i) a substrate adapted to be coupled to the portion of the structure, said substrate being flexible such that strain experienced by the portion of the structure causes relative strain in said substrate, (ii) a plurality of carbon nanotube (CNT)-based conductors operatively positioned on said substrate and arranged side-by-side to one another, said plurality of CNT-based conductors being coated with a gas-impermeable membrane to reduce pressure sensitivity of said plurality of CNT-based conductors, and (iii) at least one pair of spaced-apart electrodes electrically coupled to opposing ends of said plurality of CNT-based conductors with a portion of each of said plurality of CNT-based conductors spanning between each pair of said spaced-apart electrodes comprising a plurality of carbon nanotubes arranged end-to-end and substantially aligned along an axis; and
  means for monitoring the electrical properties of said plurality of CNT-based sensors over time so as to establish a baseline response when the portion of the structure is experiencing baseline levels of the parameter of strain and to identil$ any change in the electrical properties from the baseline response, wherein a change in the electrical properties of said plurality of CNT-based sensors is indicative of crack growth experienced by the portion of the structure.

20. A sensor assembly for detecting crack growth experienced by a structure, comprising:
  multiple close groupings of a plurality of carbon nanotube (CNT)-based sensors positioned in a dense, ordered arrangement on a portion of the structure, each of said CNT-based sensors comprising (i) a substrate adapted to be coupled to the portion of the structure, said substrate being flexible such that strain experienced by the portion of the structure causes relative strain in said substrate, (ii) a plurality of carbon nanotube (CNT)-based conductors operatively positioned on said substrate and arranged side-by-side to one another, said plurality of CNT-based conductors being coated with a gas-impermeable membrane to reduce pressure sensitivity of said plurality of CNT-based conductors, and (iii) at least one pair of spaced-apart electrodes electrically coupled to opposing ends of said plurality of CNT-based conductors with a portion of each of said plurality of CNT-based conductors spanning between each pair of said spaced-apart electrodes comprising a plurality of carbon nanotubes arranged end-to-end and substantially aligned along an axis; and
  means for monitoring the electrical properties of said plurality of CNT-based sensors over time so as to establish a baseline response when the portion of the structure is experiencing baseline levels of the parameter of strain and to identies any change in the electrical properties from the baseline response, wherein a change in the electrical properties of said plurality of CNT-based sensors is indicative of crack growth experienced by the portion of the structure.

* * * * *